United States Patent [19]

Rosenkoetter et al.

[11] Patent Number: 5,894,839
[45] Date of Patent: Apr. 20, 1999

[54] ANESTHESIA TUBE ASSEMBLY

[75] Inventors: Terry G. Rosenkoetter, Greenwood; Robert D. Richmond, Zionsville; Richard B. Hartnett, McCordsville, all of Ind.

[73] Assignee: PAR Medical, Inc., Indianapolis, Ind.

[21] Appl. No.: 08/964,252

[22] Filed: Nov. 4, 1997

Related U.S. Application Data

[62] Division of application No. 08/745,704, Nov. 12, 1996, Pat. No. 5,722,391.

[51] Int. Cl.⁶ ............................................. A61M 16/00
[52] U.S. Cl. .............................. 128/200.24; 128/202.22
[58] Field of Search ................... 128/200.24, 202.22, 128/600, 207.14, 205.12, 202.27, 205.17

[56] References Cited

U.S. PATENT DOCUMENTS

| | | |
|---|---|---|
| 3,856,051 | 12/1974 | Bain . |
| 4,007,737 | 2/1977 | Paluch . |
| 4,232,667 | 11/1980 | Chalon et al. . |
| 4,265,235 | 5/1981 | Fukunaga . |
| 5,284,160 | 2/1994 | Dryden . |
| 5,404,873 | 4/1995 | Leagre et al. . |
| 5,694,922 | 12/1997 | Palmer . |

*Primary Examiner*—John G. Weiss
*Assistant Examiner*—Charles W. Anderson
*Attorney, Agent, or Firm*—Knobbe, Martens, Olson & Bear, LLP

[57] ABSTRACT

An improved unilimb anesthesia tube assembly includes a rotatable end fitting at the patient end and inner and outer cylinders to which inner and outer unilimb tubes are secured with gas-tight seals. The invention also includes a tool and method for checking the gas-tight seals of the assembly.

8 Claims, 1 Drawing Sheet

ANESTHESIA TUBE ASSEMBLY

This application is a divisional of U.S. patent application Ser. No. 08/745,704, filed Nov. 12, 1996, now U.S. Pat. No. 5,722,391.

BACKGROUND OF THE INVENTION

In U.S. Pat. No. 4,232,667 there is disclosed a single limb or unilimb anesthesia breathing circuit in which the inspiratory and expiratory tubes are positioned with one tube inside the other. Such a construction is advantageous in preventing twisting between the two tubes which could lead to accidental disconnection as well as to reduce the clutter of anesthesia equipment in the limited surgery area. Another important advantage is improving temperature and humidity maintenance by housing the inspiratory tube entirely within the lumen of the larger diameter expiratory tube. The by-product of absorbing carbon dioxide by soda lime is heat and humidity. The heat and humidity carrying capacity of the inspiratory tube in a two-tube system is compromised due to the cooling of the uninsulated inspiratory tube. In this circuit the warm exhaled breath insulates the inspiratory tube, thus dramatically increasing the capacity of the inspiratory tube to carry heat and humidity to the patient.

Other examples of unilimb anesthesia breathing systems are disclosed in U.S. Pat. Nos. 3,856,051, 4,007,737 and 4,265,235. However, none of the aforesaid breathing tube circuits are provided with a patient end fitting to which both inner and outer tubes are secured with a gas-tight seal, and which is also fully rotatable at the patient end of the assembly. The aforesaid prior art apparatus do not have practical methods for easily and readily testing the gas-tight seal between the tubing components and the end fittings of the assembly. Such checking is not only desirable, but is often required in anesthesia apparatus check out procedures.

SUMMARY OF THE INVENTION

The anesthesia tube assembly of the present invention combines a unilimb circuit having inner and outer coaxial breathing tubes connected to a patient end fitting with a gas-tight seal of both tubes. The patient end fitting includes a fully rotatable end portion. In one embodiment, the assembly includes a gas sampling tube positioned along the interior length of the inner tube. The invention further includes means for testing the circuit for leaks between both tubes and the fittings at both ends of the tubes for gas-tight seals. The embodiment includes a tool designed for such testing by occluding both large and small diameter ports at the patient end fitting. These as well as other advantages and features of the assembly of the invention, will be evident from the following detailed description.

DETAILED DESCRIPTION OF THE PREFERRED EMBODIMENTS

Figure 1:
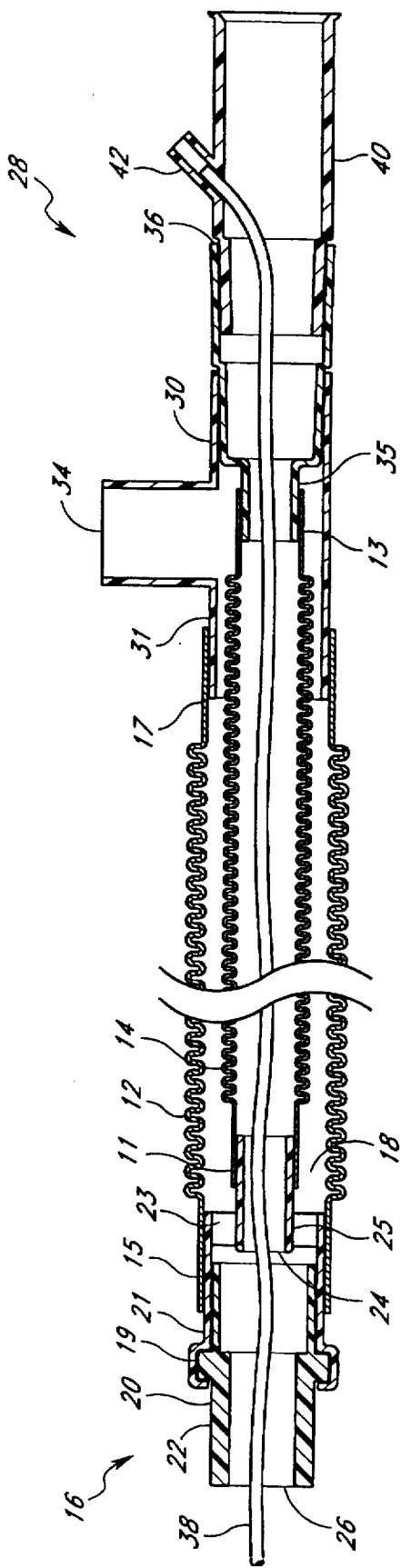
FIG. 1 is a side view of the anesthesia tube assembly of the present invention, partially broken away to illustrate features and components thereof.

FIG. 1 illustrates the anesthesia tube assembly of the present invention having an elongated hollow outer tube 12 and an elongated hollow inner tube 14 extending along the length of the interior of the outer tube 12. Both inner and outer tubes are preferably corrugated, of the type well-known to those skilled in the art used for breathing tubes and as illustrated in the aforesaid patents. The outer tube 12 is preferably 25 mm I.D. and the inner tube 14 is preferably 15 mm I.D. Such tubes are standard in the art for use in anesthesia breathing circuits. The length of the tubes may be any standard or selected tubing length such as those typically used for anesthesia or respiratory breathing circuits, well-known to those skilled in the art. The inner tube is for directing inspiratory gas from an anesthesia machine or anesthetic gas supply system, well-known in the art as described in the aforesaid patents. A first end 16 of the assembly is the patient end which is typically secured to an endotracheal tube mask elbow or an anesthesia mask. A first fitting 20 is secured both to the outer and inner tubes with gas-tight seals at the interface between the fitting and the tubes as will be explained further hereinafter. At the opposite end 28 of the assembly is a second fitting 30 which includes an expiratory gas port 34 and an inspiratory gas port 36, both of which are to be attached to tubes for directing gas to and from an anesthesia machine.

The first fitting 20 at the patient end of the assembly includes an outer cylinder 21 to which is secured the first end 15 of the outer tube in a gas-tight seal, and an inner cylinder 25 to which is attached the first end 11 of the inner tube 14, also in a gas-tight seal. The patient end fitting 20 also includes a rotatable cylindrical extension 22 which is rotatably secured to the outer cylinder 21 using a rotatable coupling 19 comprising an annular shoulder formed around extension 22 and rotatably enclosed in a circular collar as shown. Rotatable coupling 19 provides a substantially gas-tight sealing rotatable arrangement between the rotatable cylindrical extension 22 and the outer cylindrical part 21. Such a rotatable cylindrical extension component allows the assembly to be rotated or angled axially relative to a patient endotracheal tube or gas delivery mask secured at the patient end without causing stress or affecting the gas-tight seals between the assembly components or causing kinking along the inner and outer tubes. The rotatable cylindrical extension 22 may be rotatably mated to the outer cylinder portion 21 of the patient end fitting using any other suitable means including an annular wiper, flange and other mating component structures which will provide a substantially gas-tight rotatable seal between the rotatable mating surfaces and as will be understood to those skilled in the art. Such mating and substantially gas-sealing surfaces and joints may be formed using moldable plastic materials such as polyethylene, polypropylene, polyvinyl chloride, and other similar plastics commonly used for producing such anesthetic and respiratory breathing circuit components, again well-known to those skilled in the art.

The patient end fitting 20 also includes an inner concentric and coaxial cylinder 25 for being secured to inner tube 14 and for directing inspiratory gas. The inner cylinder 25 is secured to the outer cylinder 21 by a plurality of ribs 23 extending across a space between the inner and outer cylinders and defines a passageway for expired gas from the patient through the rotatable cylindrical extension 22, past the ribs 23 and into the annular expiratory passageway 18. Any number of ribs may be used to give a suitable support between the inner cylinder 25 and outer cylinder 21. The ribs are typically integrally formed at the time the outer and inner cylinders are molded. Alternatively, a wall having a sufficient number of ports to provide the expiratory passageway between the inner and outer cylinders may be used, as well as any other equivalent means for securing the inner and outer tubes with the appropriate expiratory passageway therebetween.

At the opposite end 28 of the assembly of the invention, the inner and outer tubes are secured to a second fitting 30 comprising an outer cylindrical pipe 31 and an inner coaxial and concentric cylindrical pipe 35. The outer tube 12 has a second end 17 secured to the outer cylindrical pipe 31 in a substantially gas-tight seal, and the inner tube 14 is secured at second end 13 to the inner cylindrical pipe 35, also in a gas-tight seal. Thus, both of the ends of each of the inner and outer tubes are secured in a gas-tight sealing arrangement with the respective cylindrical components of the patient end and opposite end fittings. Such bonding eliminates inner tube disconnections thereby preventing dead space variances at the patent end. Such gas-tight seals also allow the integrity of the assembly to be checked whereby any leaks can be detected. Accordingly, such an assembly avoids or prevents the potential for leaking of the expiratory gas to the room or ambient atmosphere, whereby all the patient expiratory gas is directed into the anesthetic machine, and prevents possible leaking of the expiratory gas to the inspiratory gas passageway and preventing potential contamination of the inspiratory gas. The second fitting 30 is also provided with a expiratory port 34 to be connected to a conduit (not shown) for directing the expiratory gas to a carbon dioxide absorber of an anesthesia machine. Inspiratory gas from the anesthesia machine is directed to fitting 30 at inspiratory port 36.

In the embodiment illustrated, an optional inspiratory extension pipe 40 may be used which is provided with a gas sampling port 42. In FIG. 1, there is also shown an optional embodiment of a gas sampling tube 38, which is a small-bore flexible tube for providing a gas sampling line within the circuit. The small-bore gas sampling tubing is located along the interior of inner tube 14 within unilimb breathing assembly of the present invention to reduce further clutter in the anesthesia breathing circuit area or field. The gas sampling line is typically secured using a retaining clip (not shown) within the inner tube 14 near the inner cylinder 25. Such a retaining clip is installed at the time the breathing circuit is assembled.

Figure 2:
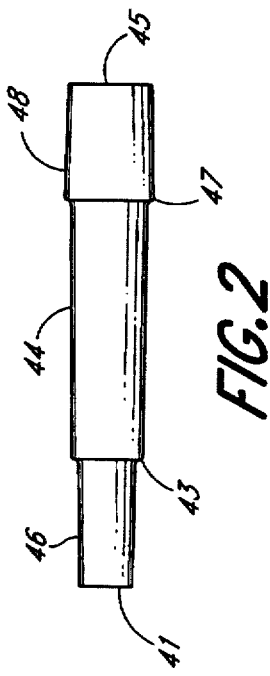
FIG. 2 is a side view of a pressure testing tool used for testing for leaks in the gas-tight seals of the assembly of FIG. 1.

In another embodiment of the invention, a device is provided for testing the integrity of the anesthesia tube assembly, specifically for checking the gas-tight seals of the inner and outer tubes with the fittings to which they are secured at both ends of the assembly. Such a device 44 is illustrated in FIG. 2 which includes a first cylindrical stopper 46 at one end and a second cylindrical stopper 48 at the opposite end. The two cylindrical stopper components have different diameters, each of which is capable of occluding and forming a gas-tight seal with one of the cylindrical components of the patient end fitting. It will be noted in FIG. 1 that port 26 of the rotatable cylindrical extension 22 has a diameter which is substantially larger than the diameter of port 24 of the inner cylinder 25. For this purpose, in the stopper device 44 shown in FIG. 2, the first cylindrical stopper 46 has a diameter capable of forming a gas-tight occlusion of port 24 of the inner cylinder 25, and second stopper 48 has a diameter capable of occluding port 26 of rotatable cylindrical extension 22. Thus, port 26 can be occluded to prevent passage of pressurized gas by inserting stopper 48, and port 24 of inner cylinder 25 can be occluded from passage of pressurized gas by inserting stopper 46. The stopper device 44 is also preferably formed so that each of the respective first and second stoppers 48 and 46 are tapered along their length. Stopper 48 is preferably gradually tapered from a smaller diameter to larger diameter from end 45 to the rear or back shoulder 47, and stopper part 46 has a gradually increased diameter from end 41 toward part line 43. Port 26 of rotatable cylindrical fitting 22 is preferably 15 mm and port 24 of inner cylinder 25 is preferably 12 mm diameter. Accordingly, the diameter of the respective stopper portions 48 and 46 of the device 44 shown in FIG. 2 will have a diameter along their respective lengths for occluding ports of these dimensions.

The integrity of the anesthesia tube assembly shown in FIG. 1 and described above may be tested as follows: after the circuit is visually checked for holes, slits or other sources of leakage, it is connected to the inspiratory and expiratory ports of an anesthesia machine with all gas flows set at zero or minimum and the pop-off valve closed. The smaller end 41 of the checking device 44 is inserted into the patient end fitting 20 and into inner cylinder 25 sufficiently to form a gas-tight seal with port 24. The breathing circuit is then pressurized to about 30 cm $H_2O$ and pressure is observed for approximately 10 seconds. The pressure checking device is then removed from the end of the circuit, and the larger end 45 of the checking device 44 is inserted into fitting 20 until port 26 is occluded and prevents the passage of pressurized gas. The breathing circuit is then pressurized to 30 cm $H_2O$ and pressure is observed for approximately 10 seconds. Thereafter, the anesthesia machine pop-off valve is opened to release the pressure. Again, such a procedure for ensuring that the gas-tight seals of the two tubes are secure with the respective end fittings will provide assurance that there is no leakage in the assembly which could interfere with the integrity of the apparatus and compromise the successful and expected performance thereof during delivery of anesthetic gas and treatment to a patient.

What is claimed is:

1. An anesthesia tube assembly comprising:

an outer tube for directing expiratory patient gas and an inner tube extending generally coaxially along the interior of said outer tube for directing inspiratory patient gas, each of said tubes having a first end secured to a first fitting and a second end secured to a second fitting, said tubes being spaced apart along their respective lengths between said first and second fittings to provide a gas passageway therealong, said first fitting comprising an outer cylinder, a concentric inner cylinder and an annular space therebetween, a plurality of ribs extending between said outer and inner cylinders for maintaining said annular space, and a rotatable cylindrical extension coaxial with and rotatably secured to said outer cylinder, said second fitting comprising an outer cylindrical pipe and a concentric inner cylindrical pipe spaced apart therefrom to provide an annular passageway, a first outlet port formed on said outer cylindrical pipe and communicating with said annular passageway, and a second outlet port extending from and communicating with said inner cylindrical pipe, wherein said first end of said outer tube is secured in a substantially gas tight seal to said outer cylinder of said first fitting and said second end of said outer tube is secured in a substantially gas tight seal to said outer cylindrical pipe of said second fitting, and said first end of said inner tube is secured in a substantially gas tight seal to said inner cylinder of said first fitting and said second end of said inner tube is secured in a substantially gas tight seal to said inner cylindrical pipe of said second fitting.

2. An anesthesia tube assembly of claim 1 including a small bore gas sampling tube extending along the interior of said inner tube between said first and second fittings.

3. An anesthesia tube assembly of claim 2 wherein a first end of said gas sampling tube extends outwardly from said first fitting through said cylindrical extension and a second end of said gas sampling tube extends outwardly from said second fitting through said second outlet port.

4. An anesthesia tube assembly of claim 3 including a hollow annular extension fitting removably secured to said second outlet port of said second fitting and having a gas sampling port extending from the exterior thereof, said second end of said gas sampling tube secured to said gas sampling port.

5. An anesthesia tube assembly of claim 1 wherein said inner and outer tubes comprise corrugated tubes.

6. An anesthesia tube assembly of claim 5 wherein said inner tube is a 15 mm I.D. tube, and said outer tube is a 25 mm I.D. tube.

7. An anesthesia tube assembly of claim 1 wherein said inner tube is a 15 mm I.D. tube, and said outer tube is a 25 mm I.D. tube.

8. A method of testing the gas tight seals of the assembly of claim 1 between said outer tube and said first and second fittings, and the gas tight seals between said inner tube and said first and second fittings, comprising:

providing a tool having a first end comprising a cylindrical stopper of a diameter sufficient to occlude said inner cylinder of said first fitting and form a substantially gas tight seal therewith, and a second end having a cylindrical stopper of a diameter sufficient to occlude said rotatable cylindrical extension of said first fitting and form a substantially gas tight seal therewith, connecting said first outlet port on said outer cylindrical extension of said second fitting and said second outlet port of said second fitting to an anesthesia machine, inserting said first end of said cylindrical stopper into said inner cylinder of said first fixture sufficiently to form a gas tight seal therein, and pressuring said tube assembly, terminating said pressurizing and observing for any pressure decay in said assembly, removing the first end of said tool from said inner cylinder of said first fitting, inserting the second end of said tool into said rotatable cylindrical extension of said first fitting, pressuring said tube assembly at said second outlet port of said second fitting, terminating said pressurizing, and observing for any pressure decay in said assembly.

* * * * *